US012427310B2

(12) United States Patent
Ironi et al.

(10) Patent No.: US 12,427,310 B2
(45) Date of Patent: *Sep. 30, 2025

(54) APPLICATION OF AN ELECTRICAL AMPLITUDE-MODULATED SIGNAL TO A SUBJECT

(71) Applicant: THERANICA BIO-ELECTRONICS LTD., Netanya (IL)

(72) Inventors: Alon Ironi, Haifa (IL); Ronen Jashek, Shoham (IL)

(73) Assignee: THERANICA BIO-ELECTRONICS LTD., Netanya (IL)

(*) Notice: Subject to any disclaimer, the term of this patent is extended or adjusted under 35 U.S.C. 154(b) by 771 days.

This patent is subject to a terminal disclaimer.

(21) Appl. No.: 17/826,367

(22) Filed: May 27, 2022

(65) Prior Publication Data
US 2022/0280791 A1 Sep. 8, 2022

Related U.S. Application Data

(63) Continuation of application No. 16/337,759, filed as application No. PCT/IL2017/051087 on Sep. 27, 2017, now Pat. No. 11,357,980.
(Continued)

(51) Int. Cl.
A61N 1/36 (2006.01)
A61N 1/04 (2006.01)

(52) U.S. Cl.
CPC ....... A61N 1/36021 (2013.01); A61N 1/0456 (2013.01); A61N 1/3603 (2017.08); A61N 1/0492 (2013.01)

(58) Field of Classification Search
CPC ...... A61N 1/0456; A61N 1/0492; A61N 1/36; A61N 1/36021; A61N 1/3603
See application file for complete search history.

(56) References Cited

U.S. PATENT DOCUMENTS 4,608,985 A 9/1986 Crish et al.
4,613,850 A 9/1986 Timmermann
(Continued)

FOREIGN PATENT DOCUMENTS

EP 2730311 5/2014
JP 2010/057804 3/2010
(Continued)

OTHER PUBLICATIONS

An International Search Report and a Written Opinion both dated Apr. 24, 2017, which issued during the prosecution of Applicant's PCT/IL2017/050028.
(Continued)

Primary Examiner — Christopher A Flory
(74) Attorney, Agent, or Firm — Sughrue Mion, PLLC

(57) ABSTRACT

Apparatus is provided that includes a set of two or more electrodes configured to be placed in electrical contact with a portion of a body of a subject, and at least one computer processor configured to drive the electrodes to apply an amplitude-modulated signal into the portion of the subject's body. The amplitude-modulated signal contains a high frequency component that acts as a carrier wave, the high frequency component having a frequency of between 80 Hz and 120 Hz, and a rectangular low frequency component that acts as a modulating component that modulates the carrier wave, the rectangular low frequency component having a frequency of between 1 Hz and 8 Hz. Other embodiments are also described.

15 Claims, 5 Drawing Sheets

Related U.S. Application Data

(60) Provisional application No. 62/412,981, filed on Oct. 26, 2016, provisional application No. 62/401,392, filed on Sep. 29, 2016, provisional application No. 62/401,380, filed on Sep. 29, 2016.

(56) References Cited

U.S. PATENT DOCUMENTS

| | | | |
|---|---|---|---|
| 4,649,936 A | 3/1987 | Ungar et al. | |
| 4,785,813 A | 11/1988 | Petrofsky | |
| 4,811,742 A | 3/1989 | Hassel et al. | |
| 4,989,605 A | 2/1991 | Rossen | |
| 5,199,430 A | 4/1993 | Fang et al. | |
| 5,215,086 A | 6/1993 | Terry, Jr. et al. | |
| 5,330,515 A | 7/1994 | Rutecki et al. | |
| 5,755,750 A | 5/1998 | Petruska et al. | |
| 5,938,690 A | 8/1999 | Law et al. | |
| 5,999,848 A | 12/1999 | Gord et al. | |
| 6,217,574 B1 | 4/2001 | Webster | |
| 6,236,889 B1* | 5/2001 | Soykan | H04B 11/00 607/30 |
| 6,249,706 B1 | 6/2001 | Sobota et al. | |
| 6,273,863 B1 | 8/2001 | Avni et al. | |
| 6,522,927 B1 | 2/2003 | Bishay et al. | |
| 6,600,954 B2 | 7/2003 | Cohen et al. | |
| 6,684,105 B2 | 1/2004 | Cohen et al. | |
| 6,741,889 B1 | 5/2004 | Holcomb | |
| 6,907,295 B2 | 6/2005 | Gross et al. | |
| 7,006,859 B1 | 2/2006 | Osorio et al. | |
| 7,155,287 B2 | 12/2006 | Gavronsky | |
| 7,200,444 B2 | 4/2007 | Gavronsky et al. | |
| 7,221,980 B2 | 5/2007 | Kotlik et al. | |
| 7,346,398 B2 | 3/2008 | Gross et al. | |
| 7,561,922 B2 | 7/2009 | Cohen et al. | |
| 7,627,384 B2 | 12/2009 | Ayal et al. | |
| 7,734,340 B2 | 6/2010 | De Ridder | |
| 7,734,355 B2 | 6/2010 | Cohen et al. | |
| 7,771,371 B2 | 8/2010 | Avni | |
| 7,778,703 B2 | 8/2010 | Gross et al. | |
| 7,998,092 B2 | 8/2011 | Avni et al. | |
| 8,295,925 B2 | 10/2012 | Brogan et al. | |
| 8,340,771 B2 | 12/2012 | Thimineur et al. | |
| 8,428,734 B2 | 4/2013 | Rigaux et al. | |
| 8,478,420 B2 | 7/2013 | Armstrong et al. | |
| 8,620,434 B2 | 12/2013 | Bodlaender et al. | |
| 8,660,651 B2 | 2/2014 | Castel et al. | |
| 8,712,546 B2 | 4/2014 | Kim et al. | |
| 8,768,428 B2 | 7/2014 | Clare et al. | |
| 8,774,925 B2 | 7/2014 | Yarnitsky | |
| 8,805,548 B2 | 8/2014 | Mignolet et al. | |
| 8,874,205 B2 | 10/2014 | Simon et al. | |
| 8,874,227 B2 | 10/2014 | Simon et al. | |
| 8,880,173 B2* | 11/2014 | DiUbaldi | A61N 1/0456 607/39 |
| 8,996,115 B2 | 3/2015 | Trier et al. | |
| 9,011,355 B2 | 4/2015 | Ehrenreich et al. | |
| 9,067,054 B2 | 6/2015 | Simon et al. | |
| 9,138,580 B2 | 9/2015 | Ignagni et al. | |
| 9,205,256 B2 | 12/2015 | Koo | |
| 9,242,085 B2 | 1/2016 | Hershey et al. | |
| 9,242,092 B2 | 1/2016 | Simon et al. | |
| 9,248,279 B2 | 2/2016 | Chen et al. | |
| 9,333,347 B2 | 5/2016 | Simon et al. | |
| 9,375,571 B2 | 6/2016 | Errico et al. | |
| 9,415,219 B2 | 8/2016 | Simon et al. | |
| 9,656,074 B2 | 5/2017 | Simon et al. | |
| 9,687,652 B2 | 6/2017 | Franke et al. | |
| 9,895,533 B2 | 2/2018 | Harpak et al. | |
| 10,213,602 B2 | 2/2019 | Ironi et al. | |
| 10,289,594 B2 | 5/2019 | Harpak et al. | |
| 10,314,501 B2* | 6/2019 | Zitnik | A61N 1/37205 |
| 10,646,400 B2 | 5/2020 | Ho | |
| 11,065,444 B2 | 7/2021 | Errico et al. | |
| 11,357,980 B2 | 6/2022 | Ironi et al. | |
| 2002/0138116 A1 | 9/2002 | Bertolucci | |
| 2003/0120271 A1 | 6/2003 | Burnside et al. | |
| 2003/0212440 A1* | 11/2003 | Boveja | A61N 1/36071 607/46 |
| 2004/0015212 A1 | 1/2004 | Huber et al. | |
| 2004/0030360 A1 | 2/2004 | Eini et al. | |
| 2004/0087838 A1 | 5/2004 | Galloway et al. | |
| 2005/0033544 A1* | 2/2005 | Brooks | G07D 7/04 702/128 |
| 2005/0118497 A1 | 6/2005 | Breen | |
| 2005/0182457 A1 | 8/2005 | Thrope et al. | |
| 2005/0234525 A1 | 10/2005 | Phillips | |
| 2005/0251061 A1 | 11/2005 | Schuler et al. | |
| 2006/0100671 A1 | 5/2006 | Ridder | |
| 2006/0149337 A1* | 7/2006 | John | A61N 1/37235 607/45 |
| 2006/0149345 A1* | 7/2006 | Boggs, II | A61N 1/36007 607/39 |
| 2006/0155345 A1 | 7/2006 | Williams et al. | |
| 2006/0206163 A1 | 9/2006 | Wahlstrand et al. | |
| 2007/0067004 A1 | 3/2007 | Boveja et al. | |
| 2007/0123952 A1 | 5/2007 | Strother et al. | |
| 2007/0203534 A1 | 8/2007 | Tapper | |
| 2007/0233203 A1 | 10/2007 | Euliano et al. | |
| 2008/0021505 A1 | 1/2008 | Hastings et al. | |
| 2008/0033504 A1 | 2/2008 | Bertolucci | |
| 2008/0065182 A1 | 3/2008 | Strother et al. | |
| 2008/0167580 A1 | 7/2008 | Avni et al. | |
| 2008/0215119 A1 | 9/2008 | Woods et al. | |
| 2009/0182393 A1 | 7/2009 | Bachinski | |
| 2009/0192406 A1 | 7/2009 | Larsen et al. | |
| 2010/0137939 A1 | 6/2010 | Liu | |
| 2010/0152817 A1* | 6/2010 | Gillbe | A61N 1/36021 607/72 |
| 2010/0249677 A1* | 9/2010 | DiUbaldi | A61H 23/0245 601/46 |
| 2010/0312166 A1 | 12/2010 | Castel | |
| 2011/0112605 A1 | 5/2011 | Fahey | |
| 2011/0215952 A1 | 9/2011 | Aria et al. | |
| 2011/0245648 A1 | 10/2011 | Hudson | |
| 2011/0264171 A1 | 10/2011 | Torgerson | |
| 2011/0276738 A1 | 11/2011 | Kim et al. | |
| 2012/0083858 A1 | 4/2012 | Yarnitsky | |
| 2012/0116478 A1 | 5/2012 | Buhlmann et al. | |
| 2012/0184801 A1 | 7/2012 | Simon et al. | |
| 2013/0085551 A1 | 4/2013 | Bachinski et al. | |
| 2013/0093501 A1 | 4/2013 | Kajimoto | |
| 2013/0158627 A1 | 6/2013 | Gozani et al. | |
| 2013/0236867 A1 | 9/2013 | Avni et al. | |
| 2013/0245486 A1 | 9/2013 | Simon et al. | |
| 2013/0338729 A1 | 12/2013 | Spector | |
| 2014/0031895 A1* | 1/2014 | Rahimi | A61N 1/36021 607/46 |
| 2014/0148870 A1 | 5/2014 | Burnett | |
| 2014/0163645 A1 | 6/2014 | Dinsmoor et al. | |
| 2014/0194946 A1 | 7/2014 | Thomas et al. | |
| 2014/0222102 A1 | 8/2014 | Lemus et al. | |
| 2014/0249601 A1 | 9/2014 | Bachinski et al. | |
| 2014/0296934 A1 | 10/2014 | Gozani et al. | |
| 2014/0324120 A1 | 10/2014 | Bogie et al. | |
| 2014/0364920 A1 | 12/2014 | Doan et al. | |
| 2014/0371814 A1 | 12/2014 | Spizzirri et al. | |
| 2015/0005852 A1 | 1/2015 | Hershey et al. | |
| 2015/0148878 A1 | 5/2015 | Yoo et al. | |
| 2015/0165186 A1 | 6/2015 | Dar et al. | |
| 2015/0174406 A1 | 6/2015 | Lamensdorf et al. | |
| 2015/0257970 A1 | 9/2015 | Mucke et al. | |
| 2015/0352357 A1 | 12/2015 | Wei et al. | |
| 2017/0001003 A1 | 1/2017 | Pivonka et al. | |
| 2017/0197077 A1 | 7/2017 | Harpak et al. | |
| 2017/0224990 A1* | 8/2017 | Goldwasser | A61N 1/0476 |
| 2017/0333715 A1* | 11/2017 | De Ridder | A61N 1/36171 |
| 2017/0368344 A1 | 12/2017 | Ironi et al. | |
| 2018/0189212 A1 | 7/2018 | Harpak et al. | |
| 2019/0001139 A1* | 1/2019 | Mishra | A61N 1/0556 |

(56) References Cited

U.S. PATENT DOCUMENTS

| | | |
|---|---|---|
| 2020/0038656 A1 | 2/2020 | Ironi et al. |
| 2022/0370787 A1 | 11/2022 | Doskocil et al. |

FOREIGN PATENT DOCUMENTS

| | | |
|---|---|---|
| JP | 2011015723 | 1/2011 |
| KR | 20110120810 | 11/2011 |
| WO | 01/10375 | 2/2001 |
| WO | 01/36051 | 5/2001 |
| WO | 02/087683 | 11/2002 |
| WO | 03/099377 | 12/2003 |
| WO | 2005/039693 | 5/2005 |
| WO | 2008/128215 | 10/2008 |
| WO | 2009/079270 | 6/2009 |
| WO | 2010/143164 | 12/2010 |
| WO | 2012/103519 A2 | 8/2012 |
| WO | 2013/134330 | 9/2013 |
| WO | 2015/042365 | 3/2015 |
| WO | 2016/025323 | 2/2016 |
| WO | 2016113661 | 7/2016 |
| WO | 2016/125087 | 8/2016 |
| WO | 2016/135604 | 9/2016 |
| WO | 2016/203356 | 12/2016 |
| WO | 2017/051412 | 3/2017 |
| WO | 2017/122195 | 7/2017 |
| WO | 2018/060997 | 4/2018 |
| WO | 2022/002467 A1 | 1/2022 |
| WO | 2022/245881 A1 | 11/2022 |

OTHER PUBLICATIONS

An International Search Report and a Written Opinion both dated Dec. 14, 2016, which issued during the prosecution of Applicant's PCT/IL2016/051043.

Degen et al., "An improved Method to continuously monitor the Electrode-Skin Impedance during Bioelectric Measurements", Proceedings of the 29th Annual International Conference of the IEEE EMBS Cite Internationale, Lyon, France, pp. 6294-6297, Aug. 23-26, 2007.

An International Search Report and a Written Opinion both dated Apr. 20, 2016, which issued during the prosecution of Applicant's PCT/IB2016/050104.

An Office Action dated Apr. 4, 2018, which issued during the prosecution of U.S. Appl. No. 15/542,553.

An Office Action dated Mar. 6, 2017, which issued during the prosecution of U.S. Appl. No. 14/992,046.

Notice of Allowance dated Sep. 24. 2018, which issued during the prosecution of U.S. Appl. No. 15/542,553.

Notice of Allowance dated Oct. 27, 2017, which issued during the prosecution of U.S. Appl. No. 14/992,046.

Slavin, Konstantin V., Hrachya Nersesyan, and Christian Wess. "Peripheral neurostimulation for treatment of intractable occipital neuralgia." Neurosurgery 58.1 (2006): 1 12-119.

Ristic, Dejan, and Jens Eilrich. "Innocuous peripheral nerve stimulation shifts stimulus-response function of painful laser stimulation in man." Neuromodulation: Technology at the Neural Interface 17.7 (2014): 686-695.

Nir, Rony-Reuven, et al. "A psychophysical study of endogenous analgesia: the role of the conditioning pain in the induction and magnitude of conditioned pain modulation." European Journal of Pain 15.5 (2011): 491-497.

Burstein, Rami, Michael F. Cutrer, and David Yarnitsky. "The development of cutaneous allodynia during a migraine attack clinical evidence for the sequential recruitment of spinal and supraspinal nociceptive neurons in migraine." Brain 123.8 (2000): 1703-1709.

Johnson MI. Transcutaneous electrical nerve stimulation (TENS) and TENS-like devices: Do they provide pain relief? Journal of Pain 2001;8:121-58.

Melzack R. Prolonged relief of pain by brief, intense transcutaneosomatic stimulation. Journal of Pain. 1975;1:357-73.

Bowman BR, Baker LL. Effects of waveform parameters on comfort during transcutaneous neuromuscular electrical stimulation. Annals of Biomedical Engineering. 1985;13:59-74.

Walsh DM, Foster NE, Baxter GD, Allen JM. Transcutaneous electrical nerve stimulation, relevance of stimulation parameters to neurophysiological and hypoalgesic effects. American Journal of Physical Medicine and Rehabilitation. 1995;74: 199-206.

Petrofsky JS, Suh HJ, Gunda S, Prowse M, Batt J. Interrelationships between body fat and skin blood flow and the current required for electrical stimulation of human muscle. Medical Engineering & Physics. 2008;30: 931-6.

Gopalkrishnan P, Sluka KA. Effect of varying frequency, intensity, and pulse duration of transcutaneous electrical nerve stimulation on primary hyperalgesia in inflamed rats. Archives of Physical Medicine and Rehabilitation. 2000;81: 984-90.

Han JS, Chen XH, Sun SL, Xu XJ, Yuan Y, Yan SC, Hao JX, Terenius L. Effect of low- and high-frequency TENS on Met-enkephalin-Arg-Phe and dynorphin A immunoreactivity in human lumbar CSF. Journal of Pain, vol. 47, Issue 3, Dec. 1991, pp. 295-298.

Melzack R, Wall PD; Pain mechanisms: a new theory; Science. 1965; 150(3699):971-979.

Tong KC, Lo SK, Cheing GL; Alternating frequencies of transcutaneous electric nerve stimulation: does it produce greater analgesic effects on mechanical and thermal pain thresholds; Archives of Physical Medicine and Rehabilitation, Oct. 2007; 88(10): 1344-9.

Chen CC, Johnson MI; An investigation into the effects of frequency-modulated transcutaneous electrical nerve stimulation (TENS) on experimentally-induced pressure pain in healthy human participants; Journal of Pain, Oct. 2009; 10(10):1029-37.

Yarnitsky D., Conditioned pain modulation (the diffuse noxious inhibitory control-like effect): its relevance for acute and chronic pain states; Current Opinion on Anaesthesiology, Oct. 2010;23(5):611-5.

Youssef A.M., V.G. Macefield V.G., Henderson L.A.; Pain inhibits pain; human brainstem mechanisms; NeuroImage 124 (2016) 54-62.

Marina De Tommaso, Olimpia Difruscolo, Michele Sardaro, Giuseppe Libro, Carla Pecoraro, Claudia Serpino, Paolo Lamberti, Paolo Livrea; Effects of remote cutaneous pain on trigeminal laser-evoked potentials in migraine patients; Journal of Headache Pain (2007) 8:167-174.

Ossipov M.H., Morimura K., Porreca F.; Descending pain modulation and chronification of pain; Current Opinion in Supportive & Palliative Care: Jun. 2014 vol. 8—Issue 2—p. 143-151.

U.S. Appl. No. 62/102,606, filed Jan. 13, 2015.

Notice of Allowance dated Nov. 26, 2018, which issued during the prosecution of U.S. Appl. No. 15/542,553.

Supplementary European Search Report dated Sep. 18, 2018, which issued during the prosecution of Applicant's European App No. 16737139.2.

Notice of Allowance dated Feb. 6, 2019, which issued during the prosecution of U.S. Appl. No. 15/736.181.

L9780 datasheet—Wide range air fuel sensor control interface. DocID026356 Rev Nov. 3, 2014. (Retrieved from the internet on Sep. 1, 2016) Retrieved from the Internet: <http://www.st.com/content/ccc/resource/technical/document/datasheet/42/c9/eb/7c/85/b9/48/fl/DM00116669.pdf/files/DM00116669.pdf/jcr:content/translations/en.DMOO 116669.pdf>STMicroelectronics NV. Nov. 30, 2014.

Communication buses and protocols for sensor networks. Sensors, 2(7), pp. 244-257. (Retrieved from the internet on Sep. 1, 2016) Retrieved from the Internet: <http://www.mdpi.net/sensors/papers/s20700244 ,pdf> Zhou, J. and Mason, A.,Dec. 31, 2002.

An International Search Report and a Written Opinion both dated Sep. 1, 2016, which issued during the prosecution of Applicant's PCT/IB2016/053463.

U.S. Appl. No. 62/180,077, filed Jun. 16, 2015.

Perttunen J, "Foot Loading in Normal and Pathological Walking," Jyväskylä: University of Jyväskylä, 2002, 86 p. (Studies in Sport, Physical Education and Health).

U.S. Appl. No. 62/221,146, filed Sep. 21, 2015.

An Invitation to pay additional fees dated Jul. 30. 2018, which issued during the prosecution of Applicant's PCT/IB2018/053385.

(56) References Cited

OTHER PUBLICATIONS

An International Search Report and a Written Opinion both dated Sep. 25, 2018, which issued during the prosecution of Applicant's PCT/IB2018/053385.

An International Search Report and a Written Opinion both dated Dec. 19, 2017, which issued during the prosecution of Applicant's PCT/IL2017/051087.

An Office Action dated Oct. 18, 2018, which issued during the prosecution of U.S. Appl. No. 15/736,181.

An International Search Report and a Written Opinion both dated Aug. 27, 2019, which issued during the prosecution of Applicant's PCTIL2019050045.

Electroacupuncture reduces Back Pain in Elderly Patients. Acupuncture Today, Aug. 2003 vol. 04, Iss 08. (Retrieved from the internet on Dec. 11, 2016) Retrieved from the Internet: <https://www.acupuncturetoday.com/pdf_out/AcupunctureToday.com-Electroacupuncture-Reduces-Back-Pain-in-Elderly-Patients-1576058026.pdf>.

U.S. Appl. No. 61/186,027, filed Jun. 11, 2009.

Granot, Michal, et al. "Determinants of endogenous analgesia magnitude in a diffuse noxious inhibitory control (DNIC) paradigm: do conditioning stimulus painfulness, gender and personality variables matter?" Pain 136.1-2 (2008): 142-149.—an Abstract.

U.S. Appl. No. 62/401,380, filed Sep. 29, 2016.

U.S. Appl. No. 62/401,392, filed Sep. 29, 2016.

U.S. Appl. No. 62/412,981, filed Oct. 26, 2016.

An Office Action dated Jul. 12, 2021, which issued during the prosecution of U.S. Appl. No. 16/337,759.

An Office Action dated Feb. 12. 2021, which issued during the prosecution of U.S. Appl. No. 16/337,759.

Notice of Allowance dated Feb. 14. 2022, which issued during the prosecution of U.S. Appl. No. 16/337,759.

An Office Action dated May 1, 2020, which issued during the prosecution of U.S. Appl. No. 15/761,614.

Notice of Allowance dated Apr. 8, 2022, which issued during the prosecution of U.S. Appl. No. 16/337,759.

Fitzpatrick, D. M., J. J. Struijk, and B. J. Andrews. "A nerve cuff design for the selective activation and blocking of myelinated nerve fibres." (1991): 906-907.

Rijkhoff, N. J. M., and Thomas Sinkjaer. "Orderly recruitment of motoneurons in an acute rabbit model." Proceedings of the 20th Annual International Conference of the IEEE Engineering in Medicine and Biology Society. vol. 20 Biomedical Engineering Towards the Year 2000 and Beyond (Cat. No. 98CH36286). vol. 5. IEEE, 1998.

* cited by examiner

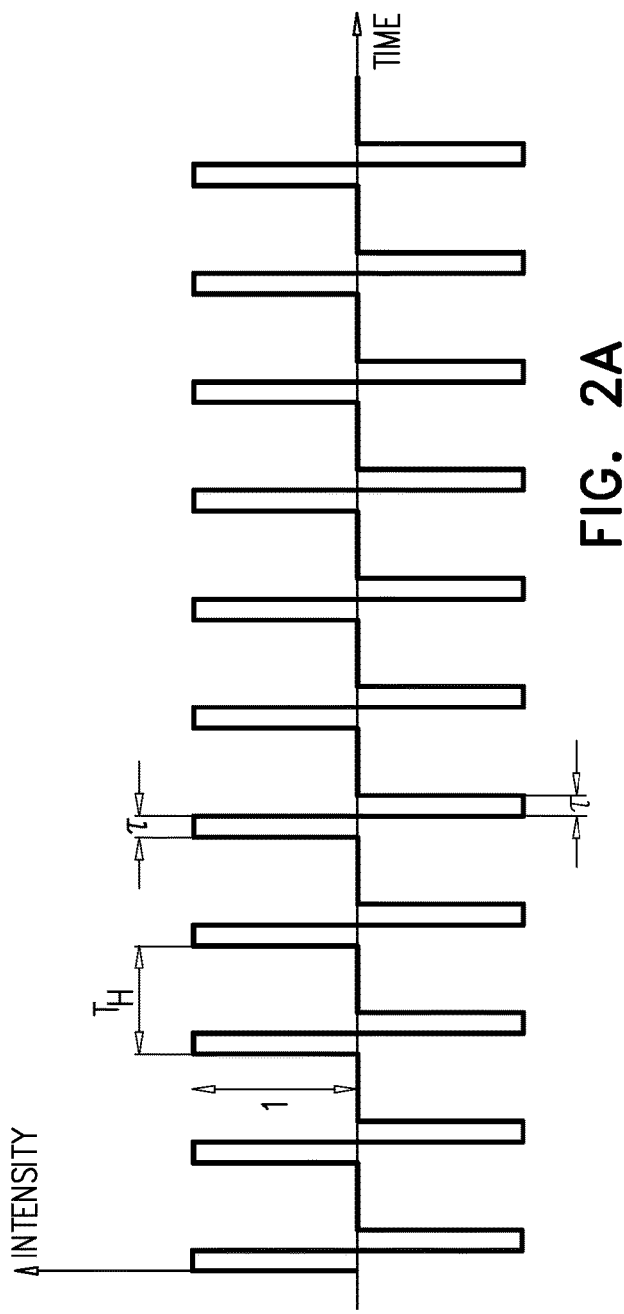
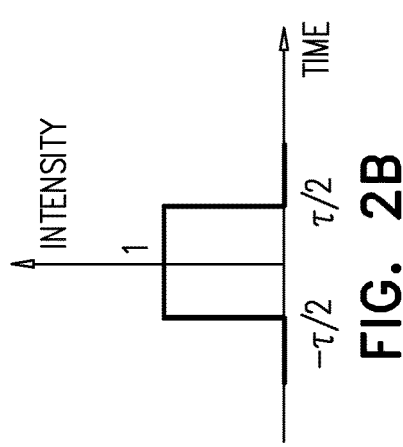

APPLICATION OF AN ELECTRICAL AMPLITUDE-MODULATED SIGNAL TO A SUBJECT

CROSS-REFERENCE TO RELATED APPLICATIONS

The present application is a continuation of U.S. application Ser. No. 16/337,759, filed Mar. 28, 2019, now U.S. Pat. No. 11,357,980, which is the US National Stage of International Application PCT/IL2017/051087, filed Sep. 27, 2016, which published as PCT Publication WO 2018/060997 and claims priority from:

U.S. Provisional Patent Application 62/401,380 to Ironi, filed Sep. 29, 2016, entitled "Apparatus and methods for Applying an Electrical Signal to a Subject;"

U.S. Provisional Patent Application 62/401,392 to Ironi, filed Sep. 29, 2016, entitled "Apparatus and methods for Applying an Electrical Signal to a Subject;" and U.S. Provisional Patent Application 62/412,981 to Ironi, filed Oct. 26, 2016, entitled "Apparatus and methods for Applying Neuromodulation to a Limb."

The above-referenced applications are incorporated herein by reference.

FIELD OF EMBODIMENTS OF THE INVENTION

Some applications of the present invention generally relate to medical apparatus and methods. Specifically, some applications of the present invention relate to apparatus and methods for electrical stimulation of a subject's body.

BACKGROUND

Migraine is a common neurovascular disorder manifesting itself in attacks of headaches that can reach a level of severe pain in many patients, leading to substantial functional impairment. To date, the pathophysiology of migraine is not fully understood. The current approach to migraine treatment is predominantly pharmacological.

Electrical nerve stimulation has been used as a possible treatment for acute pain relief, including headaches. Clinical studies have shown that two ranges of pulse frequencies (high frequency and low frequency) are especially effective for pain relief.

Neuromodulation is a term used to describe electrical nerve stimulation when it is applied for the purpose of pain relief. Some neuromodulation techniques rely upon invasive, implantable electrical stimulation for pain relief, and others apply non-invasive stimulation via the skin.

Stimulation dose (D) refers to the amount of electrical charge delivered by a stimulation device over a given time period. Generally, it is equal to the multiplication of the intensity of a single pulse (I), by the duration of that pulse (w), by the pulse frequency (f), i.e., number of pulses per second:

$$D = I * w * f$$

If I is measured in milliamps (mA), w in seconds, and f in Hertz, D is expressed in mA.

Multiplying D by the overall duration of the treatment (T) describes the total electrical charge delivered by the stimulation device to the body. The total charge may be measured, for example, in mA-seconds(mAs), milliamp-hours (mAh), or Amp-hours (Ah).

Conditioned pain modulation is a paradigm used in pain research, in which a "conditioning stimulus" (also referred to as a "secondary stimulus") is applied such as to influence the subject's perception of a "conditioned stimulus" (which is also referred to as a "primary stimulus"), which is a painful stimulus originating and/or delivered at a different body location. Painful stimuli have been shown to be inhibited using conditioned pain modulation. The source of the inhibitory process is thought to be a descending, endogenous analgesic mechanism originating in the brainstem.

Electromyography (EMG) is a known method used for recording of the neural-electrical activity of the skeletal muscles. Surface EMG (sEMG) uses electrode patches that are attached to the skin above the muscle of interest while its electrical potential is recorded.

SUMMARY OF EMBODIMENTS

For some applications, the apparatus and methods described herein are used to treat a migraine, a headache, and/or another form of pain, for example, generally in accordance with techniques described in WO 16/113661 to Ironi, which is incorporated herein by reference. Typically, in response to the subject experiencing pain (such as, a migraine a headache, or menstrual pain) in a first anatomical region, electrodes are placed on a second anatomical region of the subject body (which is a different from the first anatomical region). Electrical energy is applied to the second anatomical region by driving electrical pulses into the second anatomical region. For some applications, the electrodes are placed at location that is at a distance of more than 25 cm from the location at which the subject is experiencing pain, and the electrical energy is applied the location at which the electrodes are placed. Typically, by applying electrical energy at the second anatomical region, pain at the first anatomical region is reduced via the conditioned pain modulation mechanism.

In accordance with some applications of the present invention, a computer processor drives electrodes to apply electrical stimulation pulses to the subject's body, such that substantially for the duration of the application of the neurostimulation (e.g., more than 90 percent of the time that that the neurostimulation is being applied) the signal that is being applied contains both a high frequency component and a low frequency component. Typically, the signal that is applied is an amplitude shift keying signal, with the high frequency component acting as a carrier wave, and the low frequency component acting as a modulating wave that modulates the carrier wave. For some applications, the high frequency component has a frequency of more than 80 Hz (e.g., more than 90 Hz), and/or less than 120 Hz (e.g., less than 110 Hz), e.g., between 80 Hz and 120 Hz, or between 90 Hz and 110 Hz. For some applications, the low frequency component has a frequency of more than 1 Hz (e.g., more than 1.5 Hz), and/or less than 8 Hz (e.g., less than 4 Hz), e.g., between 1 Hz and 8 Hz, or between 1.5 Hz and 4 Hz.

Typically, the electrical pulses that are applied at the second anatomical region are configured such as to stimulate A-beta nerve fibers to a greater extent than any of the A-delta fibers, the C fibers, or motor nerve fibers. Further typically, more than 50 percent (e.g., more than 80 percent) of the applied electrical energy stimulates the A-beta fibers, and less than 20 percent (e.g., less than 10 percent, or less than 5 percent) of the applied energy stimulates any one of the A-delta fibers, the C fibers, and the motor nerve fibers. That is to say that each one of the A-delta, C, and motor categories of nerve fibers is stimulated by less than 20 percent (e.g., less than 10 percent, or less than 5 percent) of the applied energy.

Typically, by stimulating the A-beta fibers (which are non-nociceptive) to a greater extent than the A-delta fibers, or the C fibers, the electrical pulses activate the conditioned pain modulation mechanism to thereby reduce pain at the first anatomical region, but do not cause substantial local pain (or in some cases any local pain) at the second anatomical region. Despite being non-nociceptive, stimulation of the A-beta fibers is effective at activating the conditioned pain modulation mechanism. By limiting stimulation of the A-delta and C fibers, local pain that would be caused by the stimulation of the A-delta and/or C fibers is limited. Furthermore, the stimulation of the A-beta fibers inhibits the firing of the local A-delta fibers and the C fibers, such that any local pain that might have been caused by virtue of the A-delta fibers and the C fibers having been stimulated is inhibited. By limiting stimulation of the motor fibers, any involuntary movement of the subject's muscles that may be caused by electrical stimulation of these fibers is limited, thereby reducing discomfort to the subject.

1. Apparatus including:
    a set of two or more electrodes configured to be placed in electrical contact with a portion of a body of a subject; and
    at least one computer processor configured to drive the electrodes to apply an amplitude shift keying signal into the portion of the subject's body, the amplitude shift keying signal containing:
        a high frequency component that acts as a carrier wave, the high frequency component having a frequency of between 80 Hz and 120 Hz, and
        a low frequency component that acts as a modulating component that modulates the carrier wave, the low frequency component having a frequency of between 1 Hz and 8 Hz.

In some applications, the apparatus further includes a patch, the electrodes are disposed upon the patch, and the electrodes are configured to be placed in electrical contact with the portion of the subject's body by placing the patch upon the portion of the subject's body.

In some applications, the computer processor is configured to drive the electrodes to apply the amplitude shift keying signal into the portion of the subject's body by applying the low frequency signal such that:
    when a pulse of the low frequency signal is active, a current of the amplitude shift keying signal alternates between a nominal maximum and a nominal minimum of the amplitude shift keying signal, and
    when a pulse of the low frequency signal is inactive, the current of the amplitude shift keying signal alternates between the nominal maximum minus a modulation factor and the nominal minimum plus the modulation factor, the factor being between 0.3 and 0.8 of the nominal maximum.

In some applications, the computer processor is configured to drive the electrodes to apply the amplitude shift keying signal into the portion of the subject's body by:
    applying the high frequency component, the high frequency component including a biphasic pulse, and
    applying the low frequency component, the low frequency component including a monophasic pulse.

In some applications, the computer processor is configured to drive the electrodes to apply the amplitude shift keying signal into the portion of the subject's body by applying the high frequency component, the high frequency component having a base frequency, and the frequency of the high frequency component drifting from the base frequency up to 20 percent above the base frequency, and down to 20 percent below the base frequency.

There is therefore provided, in accordance with some applications of the present invention, a method including:
    applying an electrical amplitude shift keying signal to a portion of a body of a subject, via electrodes, the amplitude shift keying signal containing:
        a high frequency component that acts as a carrier wave, the high frequency component having a frequency of between 80 Hz and 120 Hz, and
        a low frequency component that acts as a modulating component that modulates the carrier wave, the low frequency component having a frequency of between 1 Hz and 8 Hz.

In some applications, applying the electrical amplitude shift keying signal to the portion of the subject's body includes applying the electrical amplitude shift keying signal to the portion of the subject's body via electrodes that are disposed on a patch that is placed onto the portion of the subject's body.

In some applications, applying the electrical amplitude shift keying signal to the portion of the subject's body includes applying the low frequency signal such that:
    when a pulse of the low frequency signal is active, a current of the amplitude shift keying signal alternates between a nominal maximum and a nominal minimum of the amplitude shift keying signal, and
    when a pulse of the low frequency signal is inactive, the current of the amplitude shift keying signal alternates between the nominal maximum minus a modulation factor and the nominal minimum plus the modulation factor, the factor being between 0.3 and 0.8 of the nominal maximum.

In some applications, applying the electrical amplitude shift keying signal to the portion of the subject's body includes:
    applying the high frequency component, the high frequency component including a biphasic pulse, and
    applying the low frequency component, the low frequency component including a monophasic pulse.

In some applications, applying the electrical amplitude shift keying signal to the portion of the subject's body includes applying the high frequency component, the high frequency component having a base frequency, and the frequency of the high frequency component drifting from the base frequency up to 20 percent above the base frequency, and down to 20 percent below the base frequency.

In some applications, the method further includes identifying the subject as suffering from a medical condition selected from the group consisting of: a migraine, a headache, and pain, and applying the electrical amplitude shift keying signal to the portion of the subject's body includes applying the electrical amplitude shift keying signal to the portion of the subject's body in response to the identifying.

In some applications:
    identifying the subject as suffering from the medical condition includes identifying the subject as suffering from pain within a first anatomical region of the subject's body; and
    applying the electrical amplitude shift keying signal to the portion of the subject's body includes applying the electrical amplitude shift keying signal to a portion of the subject's body that is within a second anatomical region, the second anatomical region being different from the first anatomical region.

In some applications:
    identifying the subject as suffering from the medical condition includes identifying the subject as suffering from pain at a first location of the subject's body; and
    applying the electrical amplitude shift keying signal to the portion of the subject's body includes applying the electrical amplitude shift keying signal to a second location of the subject's body, the second location being at a distance of more than 25 cm from the first location.

In some applications, identifying the subject as suffering from the medical condition includes identifying the subject as suffering from a migraine.

In some applications, identifying the subject as suffering from the medical condition includes identifying the subject as suffering from menstrual pain.

There is further provided, in accordance with some applications of the present invention, a method including:
    identifying a subject as suffering from pain within a first anatomical region of a body of the subject; and
    in response thereto, applying electrical energy to a second anatomical region of the subject's body by driving electrical pulses into the second anatomical region, the second anatomical region being different from the first anatomical region,
    the electrical pulses being configured such that more than 50 percent of the applied electrical energy stimulates A-beta sensory nerve fibers, and less than 20 percent of the applied electrical energy stimulates any one of A-delta sensory nerve fibers, C sensory nerve fibers, and motor nerve fibers.

The present invention will be more fully understood from the following detailed description of embodiments thereof, taken together with the drawings, in which:

BRIEF DESCRIPTION OF THE DRAWINGS

FIG. 2A is a representation of a high frequency component of an electrical stimulation signal that is applied to a subject, in accordance with some applications of the present invention;

FIG. 2B is a representation of a single monophasic pulse of a high frequency component of an electrical stimulation signal that is applied to a subject, in accordance with some applications of the present invention;

DETAILED DESCRIPTION OF EMBODIMENTS

Figure 1:
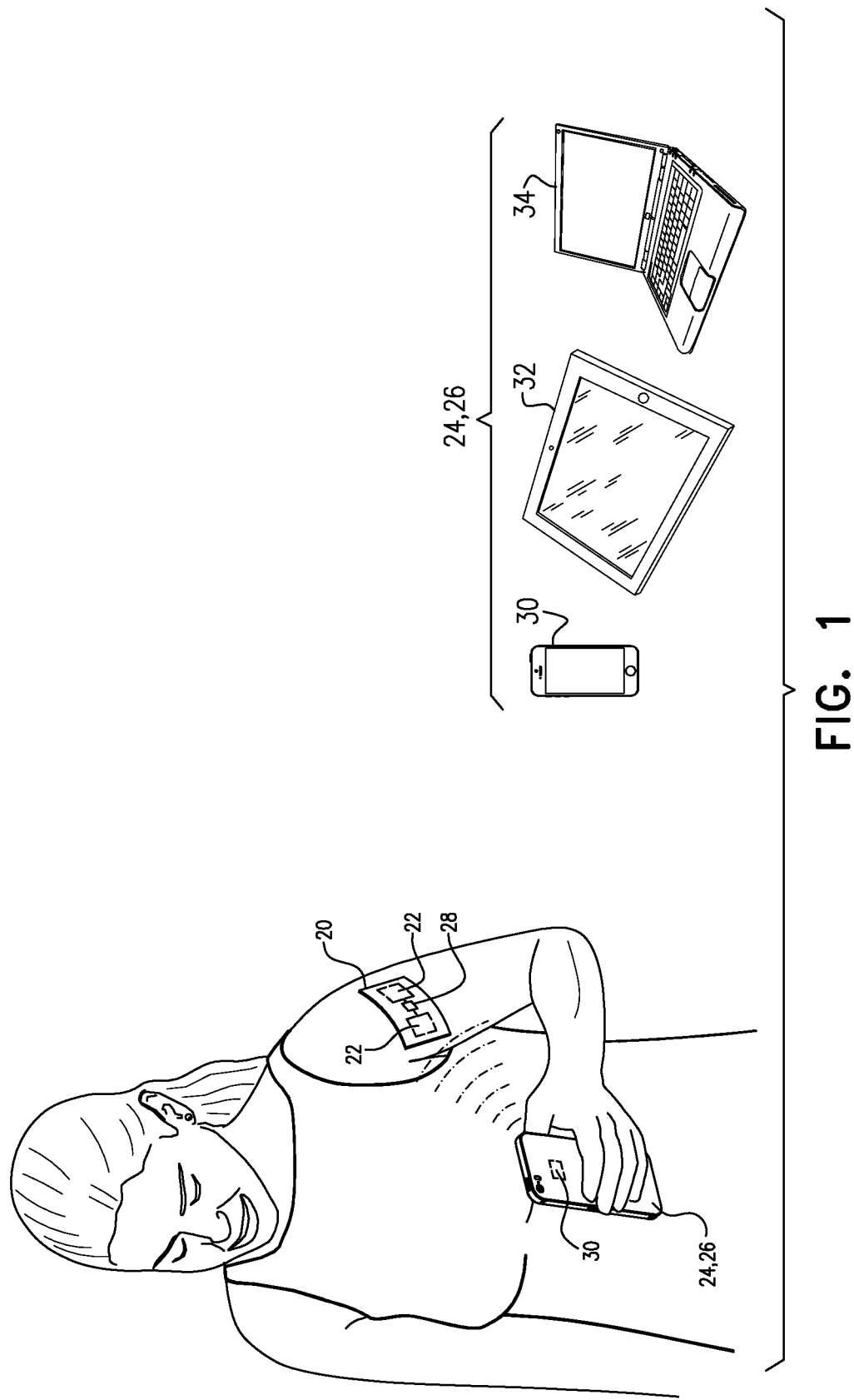
FIG. 1 is a schematic illustration of a patch having electrodes disposed thereon, a computer processor, and a user interface, in accordance with some applications of the present invention.

Reference is now made to FIG. 1, which is a schematic illustration of a patch 20 that supports electrodes 22 disposed on a subject's arm, a computer processor 24, and a user interface 26, in accordance with some applications of the present invention. For some applications, the apparatus and methods described herein are used to treat a migraine, a headache, and/or another form of pain, for example, generally in accordance with techniques described in WO 16/113661 to Ironi, which is incorporated herein by reference.

Typically, in response to the subject experiencing pain (such as, a migraine a headache, or menstrual pain) in a first anatomical region, the electrodes are placed on a second anatomical region of the subject body (which is a different from the first anatomical region). Electrical energy is applied to the second anatomical region by driving electrical pulses into the second anatomical region. For some applications, the electrodes are placed at location that is at a distance of more than 25 cm from the location at which the subject is experiencing pain, and the electrical energy is applied the location at which the electrodes are placed. Typically, by applying electrical energy at the second anatomical region, pain at the first anatomical region is reduced via the conditioned pain modulation mechanism.

For some applications, transcutaneous electrical energy is applied caudally to the neck of the subject using electrodes 22 disposed on patch 20. For some applications, upon experiencing a migraine or a headache, the subject places patch 20 upon a part of the subject's body, such as the subject's upper arm, as shown in FIG. 1. For some applications, rather than placing a patch on the subject, the subject wears a cuff, sleeve, or wrap having a plurality of electrodes 22 coupled thereto. For some applications, the electrodes are placed on a different portion of the subject's body, such as a different location on the subject's arm, on the subject's hands, legs, feet, and/or lower abdomen (e.g., in order to treat the subject for menstrual pain). Typically, the electrodes are placed in electrical contact with the subject's skin. Further typically, an electronics module 28 contained within the patch controls the electrodes, in response to control signals, which are typically wirelessly received from the computer processor.

For some applications, user interface 26 includes user interface components of one or more devices, such as a smartphone 30, a tablet device 32, and/or a personal computer 34. Typically, for such applications, computer processor 24 is the computer processor of the device. It is noted that, although FIG. 1 shows the user using a smartphone as the user interface and the computer processor, the scope of the present application includes using other devices for this purpose, e.g., tablet device 32, or personal computer 34. For some applications, electronics module 28 performs some of the computer processor functionalities that are described herein. Alternatively or additionally, the electronics module is used to facilitate communication between a computer processor of an external device (such as smartphone 30, tablet device 32, and/or personal computer 34) and the electrodes, typically using known protocols, such as Wifi, Bluetooth®, ZigBee®, or any near field communication (NFC) protocol.

Electronics module 28 typically comprises a power source, a central processing unit (CPU), typically programmed in microcode, that controls the electrodes, one or more memory units for storing the stimulation sequences during the stimulation, an impulse generator, and components for wireless communication. For some applications, the electronics module is an integrated system-on-chip (SoC). The electronics module typically includes electronic circuitry, which, by way of example, may include components such as diodes, resistors, and capacitors, etc.

For some applications, the computer processor receives an input from the subject that indicates that the subject is experiencing a headache a migraine, and/or pain, via a program or application that is run on the computer processor (e.g., a program or application that is run on smartphone 30, tablet device 32, and/or personal computer 34). In response to the input, the computer processor communicates a control signal to the electronics module. Typically, in response to receiving the control signal, the electronics module drives the electrodes to drive electrical stimulation pulses into the subject (e.g., into the subject's upper arm, as shown in FIG. 1). For some applications, the computer processor receives an input from the subject indicating a particular treatment program, and/or control stimulation parameters (such as the intensity of the stimulation) that should be provided.

For some applications, the computer processor is configured to drive the electrodes to provide stimulation to the subject to prevent the onset of headaches, migraines, or pain, before such events are sensed by the subject. For example, a stimulation treatment as described herein may be delivered at regular intervals, e.g., daily. In accordance with respective applications, the computer processor (via a program or application running on the processor) may facilitate the scheduling of such treatments, and/or may automatically alert the subject when necessary, in order to facilitate compliance with the treatment schedule.

In accordance with some applications of the present invention, the computer processor drives the electrodes to apply electrical stimulation pulses to the subject's body, such that substantially for the duration of the application of the neurostimulation (e.g., more than 90 percent of the time that that the neurostimulation is being applied) the signal that is being applied contains both a high frequency component and a low frequency component. Typically, the signal that is applied is an amplitude shift keying signal, with the high frequency component acting as a carrier wave, and the low frequency component acting as a modulating wave that modulates the carrier wave. For some applications, the high frequency component has a frequency of more than 80 Hz (e.g., more than 90 Hz), and/or less than 120 Hz (e.g., less than 110 Hz), e.g., between 80 Hz and 120 Hz, or between 90 Hz and 110 Hz. For some applications, the low frequency component has a frequency of more than 1 Hz (e.g., more than 1.5 Hz), and/or less than 8 Hz (e.g., less than 4 Hz), e.g., between 1 Hz and 8 Hz, or between 1.5 Hz and 4 Hz.

Both the high and low frequency components of the electrical simulation typically stimulate descending analgesic mechanisms. For some applications, the low frequency component primarily stimulates endorphin release, while the high frequency component primarily stimulates serotonin and/or noradrenaline release.

Reference is now made to FIG. 2A, which is a representation of a high frequency component of an electrical stimulation signal that is applied to a subject, in accordance with some applications of the present invention. Reference is also made to FIG. 2B, which is a representation of a single monophasic pulse of a high frequency component of an electrical stimulation signal that is applied to a subject, in accordance with some applications of the present invention.

Typically, the high frequency component is a train (typically, an effectively infinite train) of biphasic or monophasic pulses. For some applications, the pulses are periodic rectangular waves. For example, as shown in FIG. 2A, the high frequency component of the signal has a period $T_H$, each period including a portion during which the signal is inactive and a portion during which a biphasic pulse is applied, the biphasic pulse having a pulse duration of $2\tau$. Typically, a frequency $f_H$ of the high frequency component of the signal (which is the inverse of $T_H$) is more than 80 Hz (e.g., more than 90 Hz), and/or less than 120 Hz (e.g., less than 110 Hz), e.g., between 80 Hz and 120 Hz, or between 90 Hz and 110 Hz.

FIG. 2B is a representation of a single monophasic pulse of a high frequency component of an electrical stimulation signal that is applied to a subject, in accordance with some applications of the present invention. It is noted that, for some applications, a biphasic signal is applied (as shown in FIG. 2A), in which case the signal is composed of two such rectangles, one in the positive direction and the other in the negative direction. For some applications, a biphasic signal rather than a monophasic signal is applied, in order that the total electrical charge delivered to the body should be substantially zero.

The basic monophasic pulse ("rect(t)") is defined as follows:

$$rect(t) = \begin{cases} 1 & |t| \le \tau/2 \\ 0 & |t| > \tau/2 \end{cases}$$

where $\tau$ is the temporal width of the pulse. For some applications, the temporal width is more than 50 microseconds (e.g., more than 80 microseconds), and/or less than 150 microseconds (e.g., less than 120 microseconds), e.g., between 50 microseconds and 150 microseconds, or between 80 microseconds and 120 microseconds. The amplitude is denoted "1," this value representing the nominal amplitude of the current.

The complete waveform of the high frequency component c(t), may be described as follows:

$$c(t) = \sum_{n=0}^{N-1} rect\left(t + \frac{\tau}{2} - nT_H\right) - rect\left(t - \frac{\tau}{2} - nT_H\right)$$

where N is the number of periods. Typically, when a treatment is applied using the techniques described herein, the treatment is applied for between 10 minutes and one hour (e.g., between 15 minutes and 30 minutes). Over the treatment period, the train of pulses is effectively infinite, meaning that the value of N is effectively infinity.

Figure 3A:
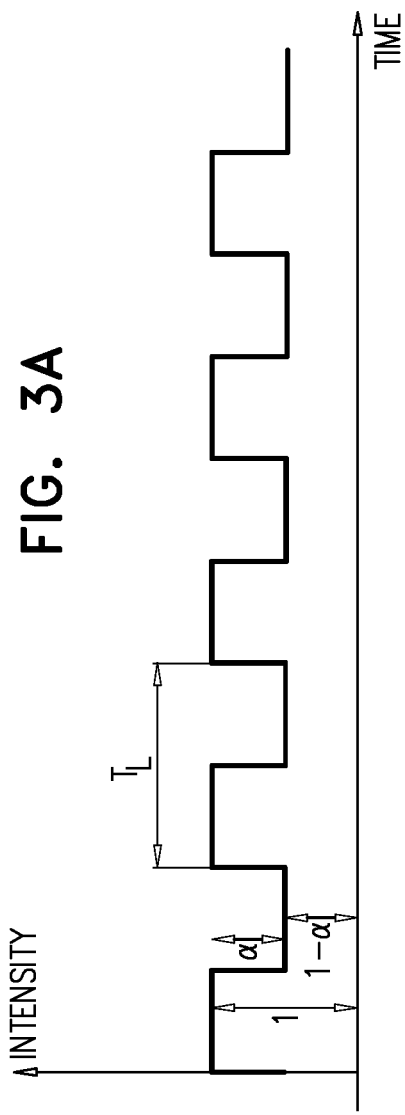
FIG. 3A is a representation of a low frequency component of an electrical stimulation signal that is applied to a subject, in accordance with some applications of the present invention.
Figure 3B:
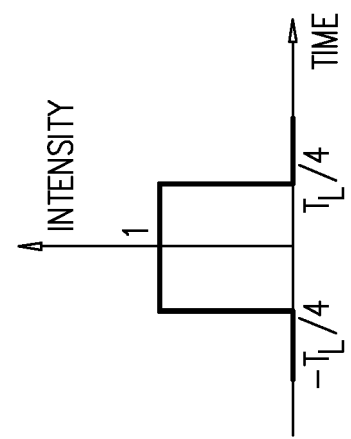
FIG. 3B which is a representation of a single monophasic pulse of a low frequency component of an electrical stimulation signal that is applied to a subject, in accordance with some applications of the present invention.

Reference is now made to FIG. 3A, which is a representation of a low frequency component of an electrical stimulation signal that is applied to a subject, in accordance with some applications of the present invention. Reference is also made to FIG. 3B, which is a representation of a single monophasic pulse of a low frequency component of an electrical stimulation signal that is applied to a subject, in accordance with some applications of the present invention.

Typically, the low frequency component is a train (typically, an effectively infinite train) of monophasic pulses. For some applications, the low frequency component has a frequency of more than 1 Hz (e.g., more than 1.5 Hz), and/or less than 8 Hz (e.g., less than 4 Hz), e.g., between 1 Hz and 8 Hz, or between 1.5 Hz and 4 Hz. For some applications, the low frequency signal has a duty cycle of 50 percent. When the pulse is inactive, the current of the low frequency signal is a given percentage (e.g., approximately 50 percent) of the maximal current of the low frequency signal, and when the pulse is active, the current of the low frequency signal is at its maximum.

FIG. 3B is a representation of a single monophasic pulse of a low frequency component of an electrical stimulation signal that is applied to a subject, in accordance with some applications of the present invention. The basic monophasic pulse ("$m_o(t)$") is defined as follows:

$$m_0(t) = \begin{cases} 1 & |t| \le T_L/4 \\ (1-\alpha) & |t| > T_L/4 \end{cases}$$

where $T_L$ is the period of the low frequency component of the signal. The amplitude 1 represents the maximum nominal amplitude of the current, which is the current when the low frequency pulse is active. The maximum nominal current is modulated by a modulation factor $\alpha$, when the pulse is inactive, $\alpha$ being a fraction, i.e., $0<\alpha<1$.

Denoting the frequency of the low frequency component of the signal by $f_L$, the complete waveform of the low frequency component m(t) may be described as follows:

$$m(t)=1-\alpha+\alpha\Sigma_{n=0}^{N-1}m_0(t-nT_L)$$

where:
N is the number of periods (which is typically effectively infinity, as described hereinabove.

Typically, the high frequency component acts as a carrier wave, and the low frequency component acts as a modulating wave that modulates the carrier wave. The modulation factor is the factor by which the low frequency wave modulates the high frequency wave, during the inactive phase of the duty cycle of the low frequency signal. In other words, when the pulse of the low frequency signal is active, the overall current of the amplitude shift keying signal alternates between the nominal maximum and the nominal minimum of the amplitude shift keying signal. When the pulse of the low frequency signal is inactive, the current of the amplitude shift keying signal alternates between nominal maximum minus the modulation factor and the nominal minimum plus the modulation factor.

If the modulation factor is small (i.e., close to 0), the impact of the modulating wave will be low, and (vice versa) if the modulating factor is large (i.e., close to 1), the impact of the modulating wave will be high. Typically, the modulating factor is more than 0.3 (e.g., more than 0.4), and/or less than 0.8 (e.g., less than 0.7), e.g., between 0.3 and 0.8, or between 0.4 and 0.7.

Figure 4:
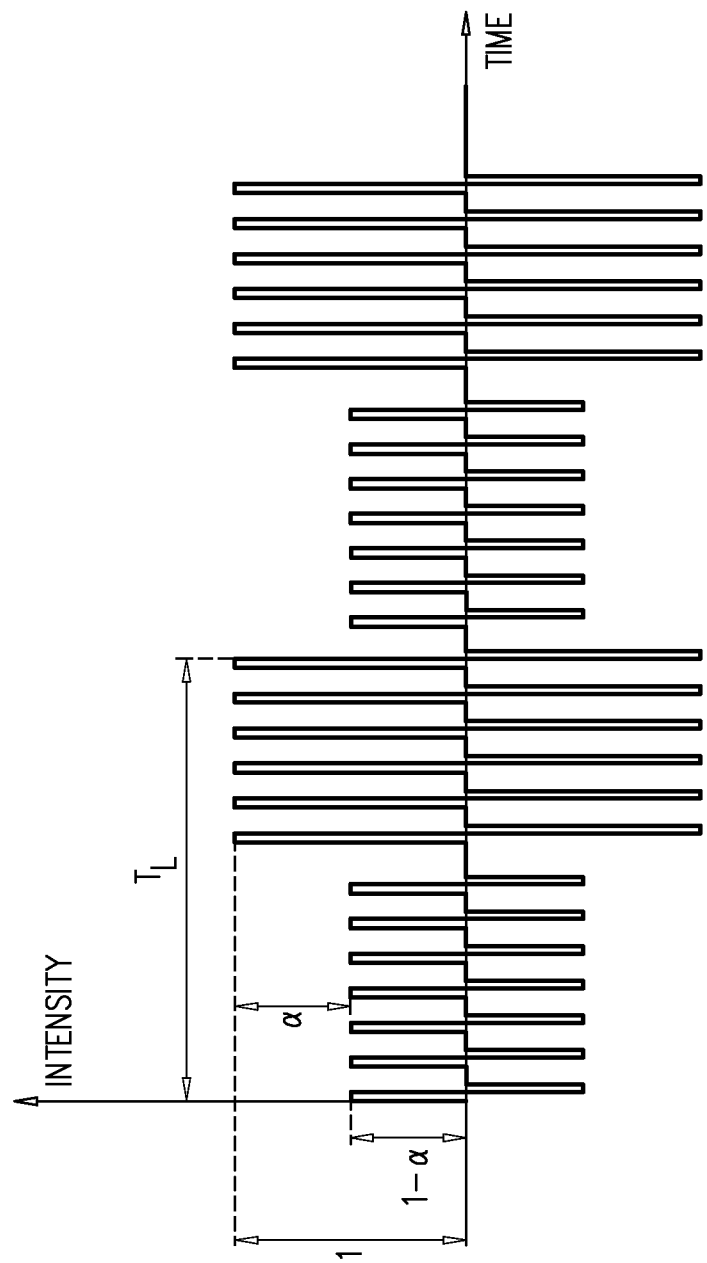
FIG. 4 shows an electrical stimulation signal that includes a high frequency component and a low frequency component that is applied to a portion of a subject's body, in accordance with some applications of the present invention.

Reference is now made to FIG. 4, which shows an electrical stimulation signal that includes a high frequency component and a low frequency component that is applied to a portion of a subject's body, in accordance with some applications of the present invention. The signal that is applied to the subject is a combination of the high frequency component (i.e., the carrier wave (c(t)), and the low frequency component (i.e., the modulating wave (m(t)). The overall waveform (s(t)) is the two waveforms multiplied by one another, and may be defined as:

$$s(t)=m(t)\cdot c(t)$$

Figure 5:
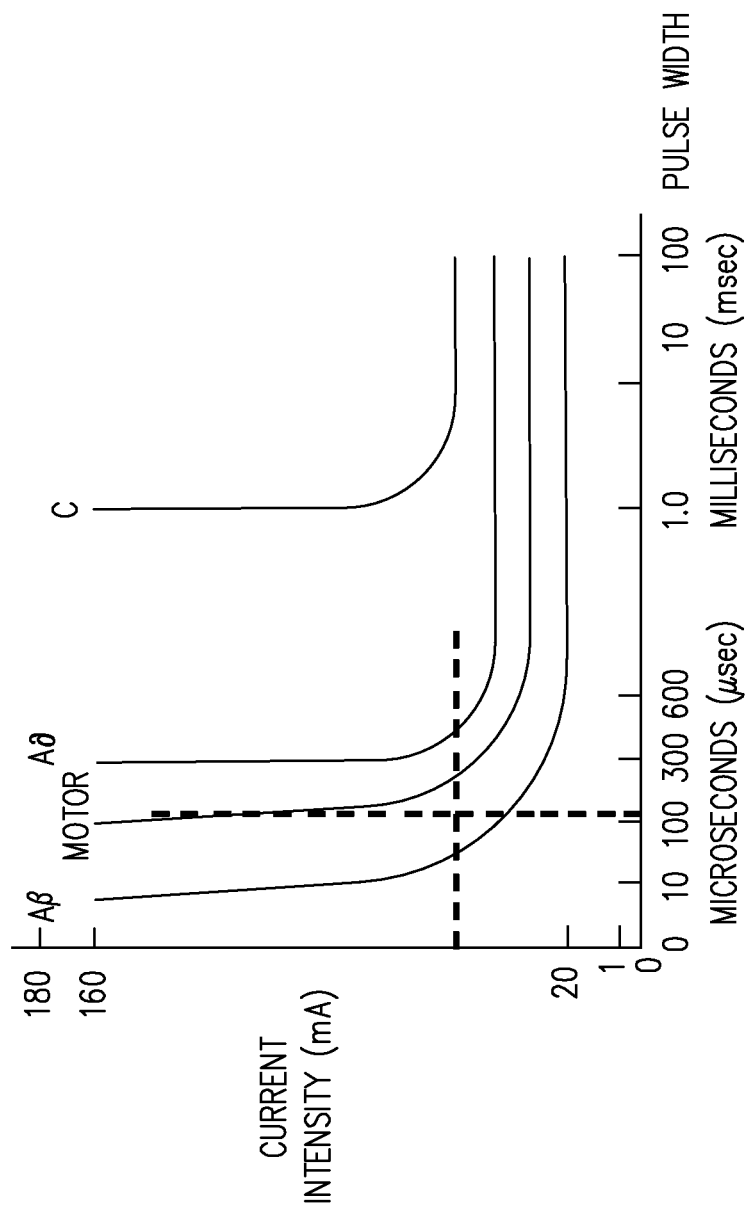
FIG. 5 is a graph showing intensity-duration threshold curves of different nerve types, based upon which parameters of electrical stimulation pulses are configured, in accordance with some applications of the present invention.

As may be observed in FIG. 5, the amplitude of the resulting waveform (s(t)):
(a) alternates between +1 and −1 when the pulse of the low frequency signal is active; and
(b) alternates between +(1-$\alpha$) and −(1-$\alpha$), when the pulse of the low frequency signal is inactive.

Thus, the change from varying between 1 and −1 to varying between (1-$\alpha$) and −(1-$\alpha$) occurs at the low frequency, $f_L$, whereas the general changes from plus to minus are at the high frequency, $f_H$. In this manner, the subject is simultaneously stimulated with both high frequency stimulation and low frequency stimulation. Both the high and low frequency components of the electrical simulation stimulate descending analgesic mechanisms. For some applications, the low frequency component primarily stimulates endorphin release, while the high frequency component primarily stimulates serotonin release.

For some applications, the high frequency component of the signal drifts between 10 percent to 20 percent below its base frequency and 10 percent to 20 percent above its base frequency. For example, starting at its base frequency, the frequency of the high frequency component of the signal may be increased by 2 Hz every minute, until it reaches 10 percent to 20 percent above its base frequency. The frequency of the high frequency component of the signal may then be decreased by 2 Hz every minute, until it reaches 10 percent to 20 percent below its base frequency. Alternatively or additionally, the frequency may be increased or decreased by approximately 10 Hz every 4 to 5 minutes. For some applications, by causing the high frequency component frequency to drift, conditioning or habituation of the subject to the stimulation is reduced. That is to say that the effect of the phenomenon whereby the perceived reception of the brain to a constant stimulus declines over time is reduced.

Reference is now made to FIG. 5, which is a graph showing intensity-duration threshold curves of different nerve types, based upon which parameters of electrical stimulation pulses are configured, in accordance with some applications of the present invention. Sensory nerve fibers in humans are typically classified to three classes, which are as follows:

1) A-beta fibers: These are large diameter fibers with high myelination. Signal propagation via these fibers is relatively fast (typically more than 40 m/s), and the activation threshold is relatively low. Such fibers are sensitive to touch, and are not sensitive to pain (i.e., non-nociceptive).

2) A-delta fibers: These are medium diameter (2-5 micron) fibers with low myelination. Signal propagation via these fibers is medium speed (typically more than 5-15 m/s), and the activation threshold is relatively high. Such fibers transmit rapid, sharp, localized pain, e.g., due to a pinch.

3) C fibers: These are small diameter (less than 2 micron) fibers with no myelination. Signal propagation via these fibers is relatively slow (typically less than 2 m/s), and the activation threshold is relatively high. Such fibers transmit slow, diffused pain signals (e.g., long term throbbing, and chronic pain messages).

As described hereinabove, in accordance with some applications of the present invention, in response to the subject experiencing pain in a first anatomical region, electrical energy is applied to the second anatomical region by driving electrical pulses into the second anatomical region. In this manner, pain at the first anatomical region is reduced via the conditioned pain modulation mechanism. Typically, the electrical pulses that are applied at the second anatomical region are configured such as to stimulate the A-beta fibers to a greater extent than any of the A-delta fibers, the C fibers, or motor nerve fibers. Further typically, more than 50 percent (e.g., more than 80 percent) of the applied electrical energy stimulates the A-beta fibers, and less than 20 percent (e.g., less than 10 percent, or less than 5 percent) of the applied energy stimulates any one of the A-delta fibers, the C fibers, and the motor nerve fibers. That is to say that each of the A-delta, C, and motor categories of nerve fibers is stimulated by less than 20 percent (e.g., less than 10 percent, or less than 5 percent) of the applied energy.

Typically, by stimulating the A-beta fibers (which are non-nociceptive) to a greater extent than the A-delta fibers, or the C fibers, the electrical pulses activate the conditioned pain modulation mechanism to thereby reduce pain at the first anatomical region, but do not cause substantial local pain (or in some cases any local pain) at the second anatomical region. Despite being non-nociceptive, stimulation of the A-beta fibers is effective at activating the conditioned pain modulation mechanism. By limiting stimulation of the A-delta and C fibers, local pain that would be caused by the stimulation of the A-delta and/or C fibers is limited. Furthermore, the stimulation of the A-beta fibers inhibits the firing of the local A-delta fibers and the C fibers, such that any local pain that might have been caused by virtue of the A-delta fibers and the C fibers having been stimulated is inhibited. By limiting stimulation of the motor fibers, any involuntary movement of the subject's muscles that may be caused by electrical stimulation of these fibers is limited, thereby reducing discomfort to the subject.

Referring again to FIG. 5, nerve fiber types have respective intensity-duration threshold curves, the intensity-duration threshold curves indicating the typical minimum threshold of current intensity and pulse duration (i.e., pulse width) that causes the respective nerve fiber types to become stimulated. Typically, the electrical pulses that are applied at the second anatomical region are configured such as to stimulate the A-beta fibers to a greater extent than any of the A-delta fibers, the C fibers, or the motor nerve fibers, by configuring the intensity and duration of the electrical pulses in accordance with the data shown in FIG. 5. Typically, both the pulse width and the current intensity of the pulses are set above the threshold levels of the A-beta nerve fibers, but below the threshold levels of A-delta fibers, C fibers, and the motor fibers.

For some applications, the pulse width is set to more than 80 microseconds (e.g., more than 120 microseconds), and/or less than 300 microseconds (e.g., less than 200 microseconds), e.g., 80-300 microseconds, or 120-200 microseconds. For some applications, the current intensity is set to more than 20 mA (e.g., more than 40 mA), and/or less than 80 mA (e.g., less than 70 mA), e.g., 20-80 mA, or 40-70 mA. An example of suitable stimulation parameters is indicated by the intersection of the horizontal and vertical dashed lines in FIG. 5. It is noted that using the above-described parameters for the electrical pulses, there may still be some stimulation of the A-delta fibers, the C fibers, and/or the motor nerve fibers. However, as described hereinabove, more than 50 percent (e.g., more than 80 percent) of the applied electrical energy stimulates the A-beta fibers, and less than 20 percent (e.g., less than 10 percent, or less than 5 percent) of the applied energy stimulates any one of the A-delta fibers, the C fibers, and the motor nerve fibers.

For some applications, electrodes are arranged on the patch (or on a different electrode supporting element, such as a cuff, etc.) such that the current density per unit area of the skin is below 3.75 mA/cm^2. In this manner, the electrical energy that is applied via the patch generates a touch sensation to the user, but does not generate a substantial amount of local pain at the location at which the patch is placed on the subject's skin.

For some applications, suitable stimulation parameters for a given user are determined interactively by the user, or a caregiver of the user. For example, the user or the caregiver may gradually increase the stimulation intensity (via the user interface) until it is evident that the intensity has reached the motor threshold (e.g., by seeing or feeling muscles activity). The user or the caregiver may then slightly reduce the stimulation intensity. As can be seen from FIG. 5, the threshold for motor nerve stimulation is above the A-beta threshold, but below the A-delta and C thresholds. Therefore, by slightly reducing the current intensity below the motor nerve stimulation threshold, the A-beta nerves will still be stimulated but the motor nerves, the A-delta nerves, and the C nerves will substantially not be stimulated.

For some applications, the stimulation parameters described with reference to FIG. 5 are combined with those described with reference to FIGS. 2A-4.

As described hereinabove, for some applications the user controls the stimulation via a user interface 26, e.g., the user interface of a device, such as a phone, as shown in FIG. 1. For some applications, during a stimulation session, a computer program (e.g., a smartphone application) allows the user to interactively control the dosage of electrical stimulation that is applied at the second anatomical region. For example, for applications in which electrodes 22 are placed on the subject's upper arm (as shown in FIG. 1), for the purpose of treating a headache and/or a migraine, the computer program may prompt the user to increase the stimulation dosage until the user feels that the stimulation is relieving headache and/or migraine symptoms. The computer program may also allow the user to indicate that the user is feeling local pain, and/or undesired movement, at the electrode placement location. In response thereto, the computer processor may prompt the user to decrease the stimulation dosage until the local pain and/or undesired movement has stopped. In this manner, via the computer processor of the user interface device, the user is able to interactively control the stimulation such that (a) the migraine or headache pain is relieved, but (b) the electrical simulation does not cause local pain and/or undesired movement at the local stimulation site.

As described hereinabove, typically, in response to the subject experiencing pain (such as, a migraine a headache, or menstrual pain) in a first anatomical region, the electrodes are placed on a second anatomical region of the subject body (which is a different from the first anatomical region). Electrical energy is applied to the second anatomical region by driving electrical pulses into the second anatomical region. By applying electrical energy at the second anatomical region, pain at the first anatomical region is reduced via the conditioned pain modulation mechanism. In order to effect the conditioned pain mechanism, the required dose of electrical stimulation that is applied must typically be sufficiently high as to invoke descending analgesic pathways.

During a period of the treatment, which may range, for example, from 20 minutes to one hour, the subject may change his/her position. Furthermore, the subject may wish to move the portion of the body (e.g., the limb) upon which electrodes 22 are placed. For example, for the application shown in FIG. 1, the subject may wish to move her arm during the treatment period. However, a stimulation dose that is applied for the pain relief therapy might be sufficiently high as to interfere with the endogenous neural stimulation sent from the brain to the motor nerves at the upper arm, or motor nerves passing through the upper arm towards the hand. Such interference might cause either difficulties in performing the required movement, and/or a sensation of discomfort.

In general, in order to reduce discomfort to the subject, the electrical stimulation dose should also be below the motor activation threshold, which differs from patient to patient, and may vary for a specific patient, depending on multiple internal and environmental factors.

Therefore, for some applications, a sensing pair of electrodes 36 are used. Typically, the sensing electrodes are placed on the skin near the location of the stimulating electrodes. For example, the sensing electrodes may be disposed on patch 20, as shown. The sensing electrodes are typically surface EMG electrodes and are configured to sense the EMG signal generated by motor nerves that enervate a muscle located in the vicinity of the electrodes 22 (e.g., under and in between the pair of electrodes 22). For some applications, the sensing electrodes are configured to sense the EMG signal generated by motor nerves that traverse a location in the vicinity of electrodes 22, but that enervate a muscle located elsewhere (e.g., motor nerves passing through the upper arm towards the hand).

Typically, in response to the signal sensed by electrodes 36, the computer processor determines changes in the energy of the EMG of the above-described motor nerves. For example, in response to the subject starting, or attempting to move a limb upon which the electrodes are placed, the computer processor detects an increase in the EMG energy. In response thereto, the computer processor reduces the stimulation dose of the electrical stimulation that is delivered via electrodes 22. (This is because the increase in the EMG energy indicates that the subject is moving or attempting to move his/her limb, and that the electrical stimulation signal may interfere with the movement or attempted movement.) Subsequently, in response to detecting that EMG energy has decreased to a given level for a given time period, the processor automatically increases the stimulation dose of the electrical stimulation. (This is because the decrease in the EMG energy indicates that the subject has stopped moving or attempting to move his/her limb.)

If the following denotation symbols are used:

$E_{EMG}$=momentary energy of the EMG as measured and calculated by the computer processor;

$E_{TH}$=a threshold level of EMG energy which the computer processor is configured to interpret as being indicative of limb movement or attempted movement (i.e., a movement threshold level);

$E_{HYS}$=a difference of EMG energy which the computer processor is configured to interpret as hysteresis when the limb is changing from motion to no motion status;

$D_{BASE}$=normal stimulation dose, when there is no limb motion, and therefore no need to reduce the dose;

$D_{MOTION}$=a reduced stimulation dose, to which to system adjusts in case of limb motion detection;

for some applications, the computer processor applies the following algorithm:

If $E_{EMG} < E_{TH}$, $D=D_{BASE}$ (I.e., normal operation, when there is no motion)

If $E_{EMG} >= E_{TH}$, $D=D_{MOTION}$, (I.e., in case of motion detection, the stimulation dose is reduced.)

Subsequent to the dose having been reduced, if $E_{EMG} < (E_{TH} - E_{HYS})$, $D=D_{BASE}$ (I.e., subsequent to motion, the stimulation dose is re-increased only if the EMG signal drops below the movement threshold level minus an amount of energy that varies with time according to a hysteresis curve.)

For some applications, the values of $E_{TH}$ and $E_{HYS}$ are determined in an individual way for each subject. For example, initially, the subject may calibrate the computer processor, during a calibration phase, using the following technique: The stimulation dose is manually adjusted until the subject is able to feel the stimulation, but the stimulation is not painful. The subject then deliberately performs a few movements with the limb, to let the computer processor record the EMG energy changes that the subject undergoes during changes from still to motion, and from motion to still.

As described hereinabove, for some applications, after the end of motion, the stimulation dose is re-increased only if the EMG signal drops below the movement threshold value minus an amount of energy that varies with time according to a hysteresis curve. The reason for subtracting the value that varies according to a hysteresis curve is to prevent the computer processor from jumping between the normal and reduced stimulation doses, as the detected EMG passes above and below the movement threshold level. This is because the computer processor jumping between the normal and reduced stimulation doses might result in unpleasant sensation for the subject.

For some applications, the value of $D_{BASE}$ is determined based upon the stimulation parameters that the subject selects during the calibration phase, as described hereinabove. The value of $D_{MOTION}$ is typically a given percentage of $D_{BASE}$, e.g., between 50 and 90 percent, or between 60 and 80 percent, of $D_{BASE}$.

For some applications, $D_{BASE}$ is initially set as ($D_{MOTOR} - \varepsilon$), where $D_{MOTOR}$ is the threshold for motor nerve activation, and $\varepsilon$ is a margin used to ensure that motor activation is avoided. Typically, dose adjustment (e.g., reduction of the electrical stimulation dose during limb motion) is performed by means of intensity adjustment. For some applications, pulse width and/or pulse frequency are adjusted. For some applications, the computer processor determines which of the parameters to adjust in order to perform dose adjustment, by initially adjusting each of the parameters, and determining the adjustment of which of the parameters leads to the lowest dose required for motor activation. The computer processor interprets this as indicating to which of the parameters the subject's neural system has greatest sensitivity, and varies the dose by adjusting this parameter.

For some applications, as an alternative to, or in addition to the computer processor automatically determining that the subject is moving or attempting to move a limb upon which the electrodes are disposed, the subject may provide an input to the computer processor indicating that he/she is moving or attempting to move the limb. Similarly, as an alternative to, or in addition to the computer processor automatically determining that the subject has finished moving or attempting to move the limb, the subject may provide an input to the computer processor indicating that he/she has finished moving or attempting to move the limb.

For some applications, the above-described electrical stimulation signals are used to provide electrical stimulation to a subject suffering from a condition other than a migraine, a headache, or pain. Furthermore, the scope of the present application includes applying electrical stimulation signals to a subject having signal characteristics as described herein, but via a different type of electrodes to those described hereinabove. For example, the stimulation may be applied via implanted electrodes, subcutaneous electrodes, and/or any other type of electrodes configured to electrically stimulate a subject.

Applications of the invention described herein can take the form of a computer program product accessible from a computer-usable or computer-readable medium (e.g., a non-transitory computer-readable medium) providing program code for use by or in connection with a computer or any instruction execution system, such as computer processor 24. For the purpose of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer-usable or computer readable medium is a non-transitory computer-usable or computer readable medium.

Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD. For some applications, cloud storage, and/or storage in a remote server is used.

A data processing system suitable for storing and/or executing program code will include at least one processor (e.g., computer processor 24) coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Network adapters may be coupled to the processor to enable the processor to become coupled to other processors or remote printers or storage devices through intervening private or public networks. Modems, cable modem and Ethernet cards are just a few of the currently available types of network adapters.

Computer program code for carrying out operations of the present invention may be written in any combination of one or more programming languages, including an object oriented programming language such as Java, Smalltalk, C++ or the like and conventional procedural programming languages, such as the C programming language or similar programming languages.

It will be understood that the methods described herein can be implemented by computer program instructions. These computer program instructions may be provided to a processor of a general purpose computer, special purpose computer, or other programmable data processing apparatus to produce a machine, such that the instructions, which execute via the processor of the computer (e.g., computer processor 24) or other programmable data processing apparatus, create means for implementing the functions/acts specified in the methods described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the methods described in the present application. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the methods described in the present application.

Computer processor 24 and the other computer processors described herein are typically hardware devices programmed with computer program instructions to produce a special purpose computer. For example, when programmed to perform the methods described herein, the computer processor typically acts as a special purpose electrical-stimulation computer processor. Typically, the operations described herein that are performed by computer processors transform the physical state of a memory, which is a real physical article, to have a different magnetic polarity, electrical charge, or the like depending on the technology of the memory that is used.

There is therefore provided, in accordance with some applications of the present invention, the following inventive concepts:

Inventive concept 1. A method comprising:
 identifying a subject as suffering from pain within a first anatomical region of a body of the subject; and
 in response thereto, applying electrical energy to a second anatomical region of the subject's body by driving electrical pulses into the second anatomical region, the second anatomical region being different from the first anatomical region,
  the electrical pulses being configured such that more than 50 percent of the applied electrical energy stimulates A-beta sensory nerve fibers, and less than 20 percent of the applied electrical energy stimulates any one of A-delta sensory nerve fibers, C sensory nerve fibers, and motor nerve fibers.

Inventive concept 2. The method according to inventive concept 1, wherein driving electrical pulses into the second anatomical region comprises driving electrical pulses into the second anatomical region, the pulses having pulse widths of 80-300 microseconds, and a current intensity of 20-80 mA.

Inventive concept 3. The method according to inventive concept 1, wherein identifying a subject as suffering from pain within the first anatomical region comprises identifying the subject as suffering from pain at a first location within the subject's body, and wherein applying electrical energy to the second anatomical region comprises applying electrical energy to a second location of the subject's body, the second location being at a distance of more than 25 cm from the first location.

Inventive concept 4. The method according to any one of inventive concepts 1-3, wherein identifying the subject as suffering from pain within the first anatomical region comprises identifying the subject as suffering from pain within an anatomical region within a head of the subject, and wherein applying electrical energy to the second anatomical region comprises applying electrical energy to a portion of the subject's body selected from the group consisting of: an arm, a leg, a hand, and a foot.

Inventive concept 5. The method according to inventive concept 4, wherein identifying the subject as suffering from pain comprises identifying the subject as suffering from a type of pain selected from the group consisting of: a headache and a migraine.

Inventive concept 6. The method according to any one of inventive concepts 1-3, wherein identifying the subject as suffering from pain within the first anatomical region comprises identifying the subject as suffering from pain within an anatomical region within a lower abdomen of the subject, and wherein applying electrical energy to the second anatomical region comprises applying electrical energy to a portion of the subject's body selected from the group consisting of: an arm, a leg, a hand, and a foot.

Inventive concept 7. The method according to inventive concept 6, wherein identifying the subject as suffering from pain comprises identifying the subject as suffering from menstrual pain.

Inventive concept 8. A method comprising:
  identifying a subject as suffering from pain within a first anatomical region of a body of the subject; and
  in response thereto, applying electrical energy to a second anatomical region of the subject's body by driving electrical pulses into the second anatomical region, the second anatomical region being different from the first anatomical region,
    the electrical pulses having pulse widths of 80-300 microseconds, and a current intensity of 20-80 mA.

Inventive concept 9. The method according to inventive concept 8, wherein driving electrical pulses into the second anatomical region comprises driving electrical pulses into the second anatomical region, the electrical pulses being configured such that more than 50 percent of the applied electrical energy stimulates A-beta sensory nerve fibers, and less than 20 percent of the applied electrical energy stimulates any one of A-delta sensory nerve fibers, C sensory nerve fibers, and motor nerve fibers.

Inventive concept 10. The method according to inventive concept 8, wherein identifying a subject as suffering from pain within the first anatomical region comprises identifying the subject as suffering from pain at a first location within the subject's body, and wherein applying electrical energy to the second anatomical region comprises applying electrical energy to a second location of the subject's body, the second location being at a distance of more than 25 cm from the first location.

Inventive concept 11. The method according to any one of inventive concepts 8-10, wherein identifying the subject as suffering from pain within the first anatomical region comprises identifying the subject as suffering from pain within an anatomical region within a head of the subject, and wherein applying electrical energy to the second anatomical region comprises applying electrical energy to a portion of the subject's body selected from the group consisting of: an arm, a leg, a hand, and a foot.

Inventive concept 12. The method according to inventive concept 11, wherein identifying the subject as suffering from pain comprises identifying the subject as suffering from a type of pain selected from the group consisting of: a headache and a migraine.

Inventive concept 13. The method according to any one of inventive concepts 8-10, wherein identifying the subject as suffering from pain within the first anatomical region comprises identifying the subject as suffering from pain within an anatomical region within a lower abdomen of the subject, and wherein applying electrical energy to the second anatomical region comprises applying electrical energy to a portion of the subject's body selected from the group consisting of: an arm, a leg, a hand, and a foot.

Inventive concept 14. The method according to inventive concept 13, wherein identifying the subject as suffering from pain comprises identifying the subject as suffering from menstrual pain.

Inventive concept 15. Apparatus comprising:
  a set of two or more electrodes configured to be placed in electrical contact with a portion of a body of a subject selected from the group consisting of: a leg, an arm, a hand, and a foot; and
  at least one computer processor configured to:
    receive an input that is indicative of the subject suffering from a condition selected from the group consisting of: a migraine, and a headache, and
    in response thereto, drive the electrodes to apply electrical energy to the selected portion of the subject's body, the electrical pulses having pulse widths of 80-300 microseconds, and a current intensity of 20-80 mA.

Inventive concept 16. The apparatus according to inventive concept 15, further comprising a patch, wherein the electrodes are disposed upon the patch and the electrodes are configured to be placed in electrical contact with the selected portion of the subject's body by placing the patch upon the selected portion of the subject's body.

Inventive concept 17. A method comprising:
  identifying a subject as suffering from pain within a first anatomical region of a body of the subject;
  in response thereto, applying an electrical stimulation signal to a second anatomical region of the subject's body by driving electrical pulses into the second anatomical region, the second anatomical region being different from the first anatomical region, the electrical stimulation signal being applied at a given dosage;
  during the application of the electrical stimulation signal, detecting a signal that is indicative of muscular movement at the second anatomical region; and
  in response thereto, automatically reducing the dosage of the electrical stimulation signal to a dosage that is less than the given dosage.

Inventive concept 18. Apparatus comprising:
  a set of two or more simulation electrodes configured to be placed in electrical contact with a portion of a body of a subject selected from the group consisting of: a leg, an arm, a hand, and a foot;
  a set of two or more sensing electrodes configured to detect an electrical signal of the selected portion of the subject's body, and to generate a detection signal, in response thereto; and
  at least one computer processor configured to:
    receive an input that is indicative of the subject suffering from a condition selected from the group consisting of: a migraine, and a headache,
    in response thereto, drive the stimulation electrodes to apply an electrical stimulation signal to the selected portion of the subject's body, the electrical stimulation signal being applied at a given dosage;
    during the application of the electrical stimulation signal, determine that the detection signal is indicative of muscular movement at the selected portion of the subject's body; and
    in response thereto, automatically reduce the dosage of the electrical stimulation signal to a dosage that is less than the given dosage.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
a set of two or more electrodes configured to be placed in electrical contact with a portion of a body of a subject; and
at least one computer processor configured to drive the electrodes to apply an amplitude-modulated signal into the portion of the subject's body, the amplitude-modulated signal containing:
a high frequency component that acts as a carrier wave, the high frequency component having a frequency of between 80 Hz and 120 Hz, and
a rectangular low frequency component that acts as a modulating component that modulates the carrier wave, the rectangular low frequency component having a frequency of between 1 Hz and 8 Hz.

2. The apparatus according to claim 1, further comprising a patch, wherein the electrodes are disposed upon the patch and the electrodes are configured to be placed in electrical contact with the portion of the subject's body by placing the patch upon the portion of the subject's body.

3. The apparatus according to claim 1, wherein the computer processor is configured to drive the electrodes to apply the amplitude-modulated signal into the portion of the subject's body by:
applying the high frequency component, the high frequency component including a biphasic pulse, and
applying the rectangular low frequency component, the rectangular low frequency component including a monophasic pulse.

4. The apparatus according to claim 1, wherein the computer processor is configured to drive the electrodes to apply the amplitude-modulated signal into the portion of the subject's body by applying the high frequency component, the high frequency component having a base frequency, and the frequency of the high frequency component drifting from the base frequency up to 20 percent above the base frequency, and down to 20 percent below the base frequency.

5. The apparatus according to claim 1, wherein the at least one computer processor is configured to drive the electrodes to apply the amplitude-modulated signal such that the high frequency component includes rectangular pulses.

6. A method comprising:
applying an electrical amplitude-modulated signal to a portion of a body of a subject, via electrodes, the amplitude-modulated signal containing:
a high frequency component that acts as a carrier wave, the high frequency component having a frequency of between 80 Hz and 120 Hz, and
a rectangular low frequency component that acts as a modulating component that modulates the carrier wave, the rectangular low frequency component having a frequency of between 1 Hz and 8 Hz.

7. The method according to claim 6, wherein applying the electrical amplitude-modulated signal to the portion of the subject's body comprises applying the electrical amplitude-modulated signal to the portion of the subject's body via electrodes that are disposed on a patch that is placed onto the portion of the subject's body.

8. The method according to claim 6, wherein applying the electrical amplitude-modulated signal to the portion of the subject's body comprises:
applying the high frequency component, the high frequency component including a biphasic pulse, and
applying the rectangular low frequency component, the rectangular low frequency component including a monophasic pulse.

9. The method according to claim 6, wherein applying the electrical amplitude-modulated signal to the portion of the subject's body comprises applying the high frequency component, the high frequency component having a base frequency, and the frequency of the high frequency component drifting from the base frequency up to 20 percent above the base frequency, and down to 20 percent below the base frequency.

10. The method according to claim 6, further comprising identifying the subject as suffering from a medical condition selected from the group consisting of: a migraine, a headache, and pain, wherein applying the electrical amplitude-modulated signal to the portion of the subject's body comprises applying the electrical amplitude-modulated signal to the portion of the subject's body in response to the identifying.

11. The method according to claim 10,
wherein identifying the subject as suffering from the medical condition comprises identifying the subject as suffering from pain within a first anatomical region of the subject's body; and
wherein applying the electrical amplitude-modulated signal to the portion of the subject's body comprises applying the electrical amplitude-modulated signal to a portion of the subject's body that is within a second anatomical region, the second anatomical region being different from the first anatomical region.

12. The method according to claim 10,
wherein identifying the subject as suffering from the medical condition comprises identifying the subject as suffering from pain at a first location of the subject's body; and
wherein applying the electrical amplitude-modulated signal to the portion of the subject's body comprises applying the electrical amplitude-modulated signal to a second location of the subject's body, the second location being at a distance of more than 25 cm from the first location.

13. The method according to claim 10, wherein identifying the subject as suffering from the medical condition comprises identifying the subject as suffering from a migraine.

14. The method according to claim 10, wherein identifying the subject as suffering from the medical condition comprises identifying the subject as suffering from menstrual pain.

15. The method according to claim 6, wherein applying the electrical amplitude-modulated signal comprises applying the electrical amplitude-modulated signal such that the high frequency component includes rectangular pulses.

* * * * *